(12) United States Patent
Wang et al.

(10) Patent No.: US 9,873,874 B2
(45) Date of Patent: Jan. 23, 2018

(54) HIGH-YIELD METHOD FOR RAPIDLY CONJUGATING RIBONUCLEIC ACID (RNA) TO DIETHYLENETRIAMINE PENTAACETIC ACID (DTPA)

(71) Applicant: Institute of Nuclear Energy Research, Atomic Energy Council, Executive Yuan, R.O.C., Taoyuan (TW)

(72) Inventors: Mei-Hui Wang, Taoyuan (TW); Chia-Yu Hu, Taoyuan (TW); Chun-Hung Yang, Taoyuan (TW)

(73) Assignee: INSTITUTE OF NUCLEAR ENERGY RESEARCH, ATOMIC ENERGY COUNCIL, EXECUTIVE YUAN, R.O.C., Taoyuan (TW)

( * ) Notice: Subject to any disclaimer, the term of this patent is extended or adjusted under 35 U.S.C. 154(b) by 0 days.

(21) Appl. No.: 15/212,697

(22) Filed: Jul. 18, 2016

(65) Prior Publication Data

US 2017/0183651 A1 Jun. 29, 2017

(30) Foreign Application Priority Data

Dec. 25, 2015 (TW) .............................. 104143832 A

(51) Int. Cl.
*C12N 15/113* (2010.01)
(52) U.S. Cl.
CPC .................................. *C12N 15/113* (2013.01)

(58) Field of Classification Search
None
See application file for complete search history.

(56) References Cited

PUBLICATIONS

Hnatowich, The Journal of Nuclear Medicine, vol. 36, No. 12, Dec. 1995.*
Zhonghan Li et al., Therapeutic targeting of microRNAs: current status and future challenges, Nature Reviews Drug Discovery, 2014, 622-638, 13.
Laurence Perreux et al., Solvent-free preparation of amides from acids and primary amines under microwave irradiation, Tetrahedron, 2002, 2155-2162, 58.
Edith Gelens et al., An atom efficient and solvent-free synthesis of structurally diverse amides using microwaves, Tetrahedron Letters, 2005, 3751-3754, 46.
Olivia M. Merkel et al., In vivo SPECT and real-time gamma camera imaging of biodistribution and pharmacokinetics of siRNA delivery using an optimized radiolabeling and purification procedure, Bioconjugate Chem., 2009, 174-182, 20.

* cited by examiner

*Primary Examiner* — Layla D Berry
(74) *Attorney, Agent, or Firm* — Locke Lord LLP; Tim Tingkang Xia, Esq.

(57) ABSTRACT

The invention discloses a high-yield method for preparing a ribonucleic acid (RNA)-diethyltriamine pentaacetic acid (DTPA) conjugate. The conjugate is prepared by conjugating a RNA or locked nucleic acid (LNA) having an amino group to p-isothiocyanate benzyl-DTPA (SCN-Bn-DTPA) or DTPA anhydride with heating under microwave.

5 Claims, 7 Drawing Sheets

HIGH-YIELD METHOD FOR RAPIDLY CONJUGATING RIBONUCLEIC ACID (RNA) TO DIETHYLENETRIAMINE PENTAACETIC ACID (DTPA)

CROSS-REFERENCE TO RELATED APPLICATION

This application also claims priority to Taiwan Patent Application No. 104143832 filed in the Taiwan Patent Office on Dec. 25, 2015, the entire content of which is incorporated herein by reference.

TECHNICAL FIELD

The present disclosure relates to a method for preparing a ribonucleic acid (RNA)-diethylenetriamine pentaacetic acid (DTPA) conjugate, and more particularly to a method for preparing a precursor useful in imaging of a RNA molecule.

BACKGROUND miRNAs are endogenous small RNAs (having about 22 nucleotides in sequence), which may specifically bind to genes of particular sequences to regulate the gene expression. At present, numerous studies show that miRNA is associated with the induction of many diseases in human, including cancers, viral infections, cardiovascular diseases, and inflammatory reactions. Control or inhibition of miRNA may provide a strategy for disease treatment. Due to its low toxicity, there have been many treatment strategies with miRNA targeting anti-sense oligonucleotides under clinical trial. The miRNA targeting treatment strategy includes blocking the function of miRNA with some chemically modified anti-sense oligonucleotides, in which the modification is mainly carried out at carbon No. 2 of ribose, for example, replacing the hydroxyl group at carbon No. 2 by 2'-fluoro, 2'-oxy-methyl, 2'-oxyethyl alcohol, 2'-O,4'-C methylene (also referred to as locked nucleic acid (LNA)), 3'-oxyphosphorus sulfide, 2'-deoxyribonucleic acid, and the like. Many anti-sense oligonucleotides successfully enter phase II clinical trial, and have shown to have a safety. For example, the anti-sense oligonucleotide miravirsen (anti-miR122) for treating hepatitis C is a 2'-LNA having 15 nucleotides and 3'-oxyphosphorus sulfide, which can reduce the amount of hepatitis C virus by 100 times in a preclinical trial in chimpanzees, exhibits no adverse effects in phase I clinical trial, and has entered phase II clinical trial (Nature Reviews of Drug Discovery 13, 634, 2014.).

The miRNA targeting anti-sense oligonucleotide therapeutic agent needs to be subjected to bio-distribution and pharmacodynamic test before clinical use. Traditionally, the conventional biodistribution method was done with sacrificed mice, the organs are removed and broken down, and then miRNA is extracted and quantified by enzymatic immunoassay. The major difficulty is the cost. At present, the chemically modified anti-sense oligonucleotide is expensive. It is economic to evaluate the bio-distribution by in-vivo imaging with radioactive label. The metal indium-111 is one of the radioactive isotopes typically used in clinic, which has a medium half-life of 2.8 days and is a good choice in the case of unknown pharmacokinetics of the drug.

Amide bond formation is generally achieved by activating an acid group with an anhydride, an acid ester or with the aid of some conjugating agent such as carbodiimide.

Perreux et al. (Tetrahedron 58(2002), 2155-2162) and Gelens et al (Tetrahedron Letters 2005, 46(21) 3751-3754) report that with the aid of microwave radiation, amide bond formation of benzoic acid with benzylamine is achievable, whereby the amide bonding of 10 mL of the reactant carboxylic acid at mmol level with amine is accomplished, and the yield is increased from the conventional 17% to 80%. However, this has not been used with trace amount of ribonucleic acid, particularly RNA at nmol level. To conjugate a RNA to DTPA, the RNA must have an amino group. Therefore, a long C6-amino arm is terminally added to RNA. The DTPA used is DTPA anhydride or p-isothiocyanate benzyl-DTPA (SCN-Bn-DTPA), such that amide bonding may be carried out under a basic condition. At present, there are few literatures reporting the radioactive label of chemically modified anti-sense oligonucleotide. The DTPA chelating agent generally sequesters indium-111, and used as an imaging agent, to visualize the bio-distribution of the RNA. However, the conventional method suffers from many drawbacks, including long reaction time and low yield.

LNA is known to have the optimum stability among all the chemically modified anti-sense oligonucleotides. There are few studies on imaging of and conjugation of LNA to DTPA. Olivia M. (Bioconjugate Chem. 2009, 20, 174-182) reports that a RNA-DTPA conjugate is successfully formed by reacting 10 nmol RNA in 0.1 M sodium hydroxide (pH 8.0-8.5) with 50 times of p-SCN-Bn-DTPA. However, the yield of the conjugation product is low and is only 32%. Even when the reaction time is extended from 45 min to 3 hrs, the yield of the RNA-DTPA conjugate cannot be increased, because the extended reaction time is unfavorable to the stability of RNA, due to the increased potential of labile breakage. In this regard, attempts are made to react overnight with heating. As analyzed by Matrix-Assisted Laser Desorption/Ionization Time of Flight Mass Spectrometry (MALDI-TOF), the RNA cannot be completely conjugated to DTPA even more DTPA (50 times) is added. Although the compounds with different molecular weights may be separated by the so-called gel chromatography, the molecular weight of the RNA-DTPA conjugate only slightly differs from that of RNA by about 390-542, and thus the purification is difficult. The disadvantages of long reaction time and incomplete conjugation of RNA to DTPA limit the development of RNA in molecular imaging technology.

SUMMARY

To overcome the bottleneck in conjugating a RNA to DTPA, an objective of the present invention is to provide a high-yield method for rapidly conjugating a RNA to DTPA, and more particularly, conjugating a RNA having an amino group to p-isothiocyanate benzyl-DTPA (SCN-Bn-DTPA) or DTPA anhydride through an amido group with heating under microwave.

The high-yield method for rapidly conjugating a RNA to DTPA according to the present invention comprises reacting the RNA and DTPA for 5 min at 94° C. in an aqueous sodium bicarbonate solution or for 10 min at 75° C. in a 2-10% sodium bicarbonate solution in DMSO, with heating under microwave.

In an embodiment, the pH of the sodium bicarbonate solution is substantially 8.0-8.5.

In an embodiment, the RNA is a locked nucleic acid (LNA) or DNA having an amino group.

In an embodiment, the DTPA is DTPA anhydride or p-isothiocyanate benzyl-DTPA (SCN-Bn-DTPA).

In an embodiment, the RNA is at nmol level.

In an embodiment, the reaction is complete at a reaction volume of only 50 μL.

In an embodiment, the reaction yield of the RNA-DTPA conjugate is 100%.

In the high-yield method for rapidly conjugating a RNA to DTPA according to the present invention, with the aid of heating under microwave, the RNA at nmol level is facilitated to conjugate to DTPA in 10 min with a conjugation yield of up to 100%. The novel RNA-DTPA conjugate obtained in the present invention has a high conjugation yield and a high reproducibility, and the RNA-DTPA conjugate can be produced stably with a yield of 100%. The conjugate is useful as a precursor of a radioactive label for later molecular imaging.

The descriptions of the summary above and the embodiments below are provided for exemplifying and illustrating the principle of the present invention, and further explaining the scope of the claims of the present invention.

DETAILED DESCRIPTION OF DISCLOSED EMBODIMENTS

The particular features and advantages of the present invention are described in detail in embodiments below, for better understanding and implementing the technical contents of the present invention by any one of skill in the art. Relevant objectives and advantages of the present invention are apparent to those skilled in the art from the disclosure, claims, and accompanying drawings herein. The embodiments below are provided for elucidating the idea of the present invention in further detail, instead of limiting the scope of the present invention in any way.

The features and implementations of the present invention are described in detail by way of most preferred examples.

EXAMPLE 1

Figure 1:
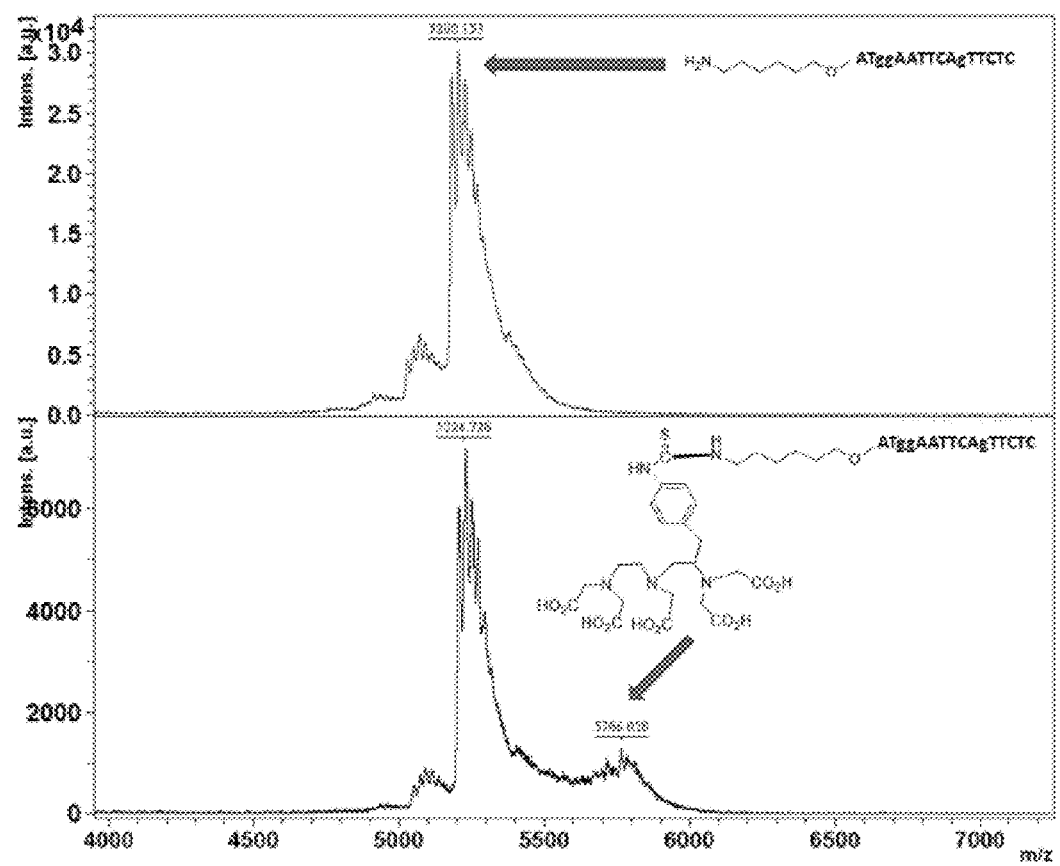
FIG. 1 is a MALDI-TOF mass spectrum of a p-SCN-Bn-DTPA-DNA conjugate prepared through a conventional heating method.

Conventional Conjugation of p-SCN-Bn-DTPA to DNA 32.4 nmol of a 16 mer single-stranded DNA (5'-ATG-GAATTCAGTTCTC-3'; SEQ ID: NO. 1) was dissolved in 20 µL of 0.5 M NaHCO$_3$ solution. Then, 36 µL of DMSO (dimethyl sulfoxide) was added, which contained p-SCN-Bn-DTPA (2-(4-isothiocyanatobenzyl)-diethylenetriaminepentaacetic acid) in moles of 50 times of that of the DNA. Subsequently, the reaction was agitated overnight (for more than 12 hrs) at room temperature. Next, the resulting product was centrifuged for 3 min at 1000 g, and then passed through a Centri·Pure MINI SEQ Z-25 size exclusion column (a desalting column, manufactured by emp BIOTECH). Then, the eluate was collected, that is, DTPA-DNA. MS analysis of the product was carried out. The process was briefly as follows. 0.5 µL of the purified DTPA-DNA and 1.5 µL of 3-Hydroxypicolinic acid (3-HPA) were used as a matrix, mixed uniformly, dotted on a sample disc, naturally air dried, and determined for the molecular weight of DTPA-DNA by Matrix-Assisted Laser Desorption/Ionization Time of Flight Mass Spectrometry (MALDI-TOF). The molecular weight of the 16mer single-stranded DNA is determined to be 5200 Da by MS analysis. After conjugation to p-SCN-Bn-DTPA, the molecular weight peak is shown to shift to 5766 Da by MS analysis. However, there is a large amount of DNA unconjugated to p-SCN-Bn-DTPA, as shown in FIG. 1.

EXAMPLE 2

Figure 2:
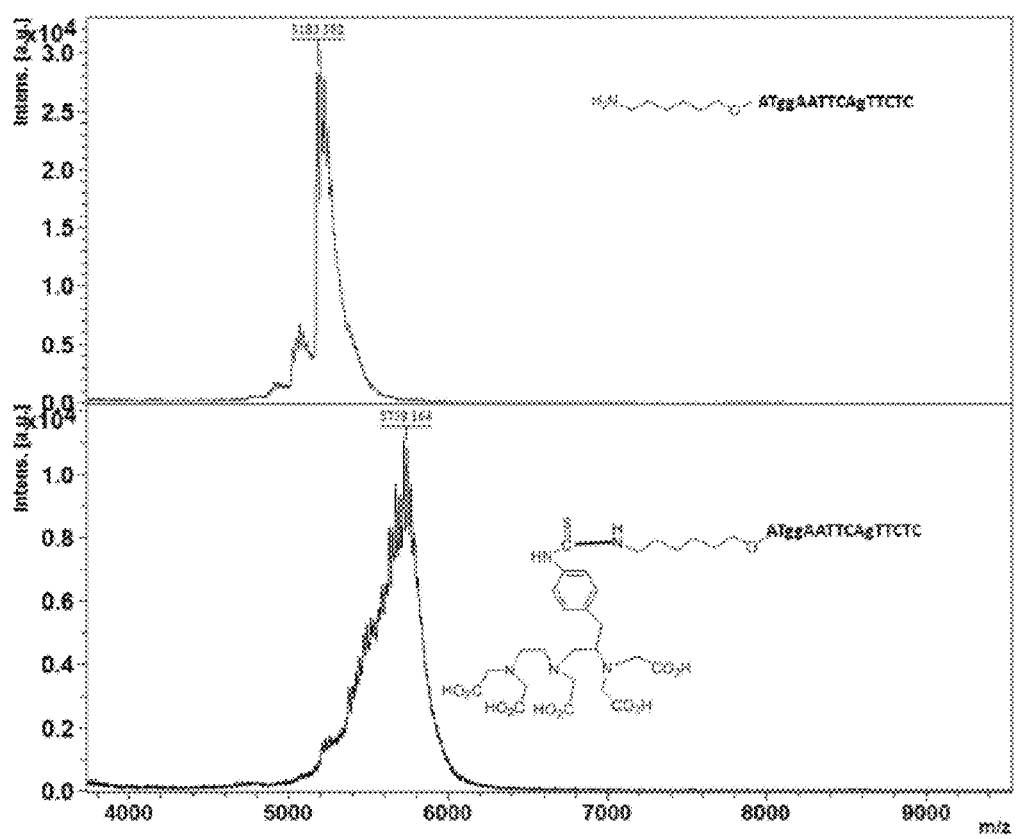
FIG. 2 is a MALDI-TOF mass spectrum of a p-SCN-Bn-DTPA-DNA conjugate prepared in DMSO with heating under microwave.
Figure 7A:
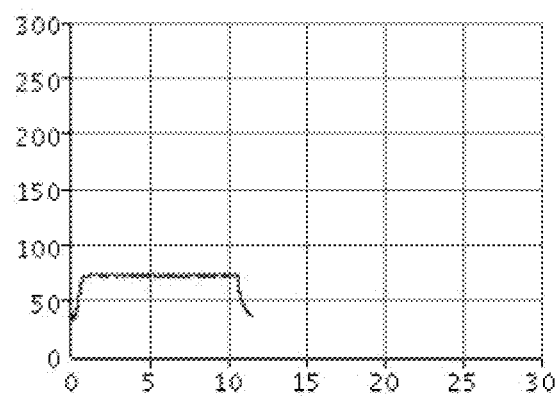
FIGS. 7A and 7B show variations in reaction temperature and power (75° C., 10 min) upon heating under microwave.
Figure 7B:
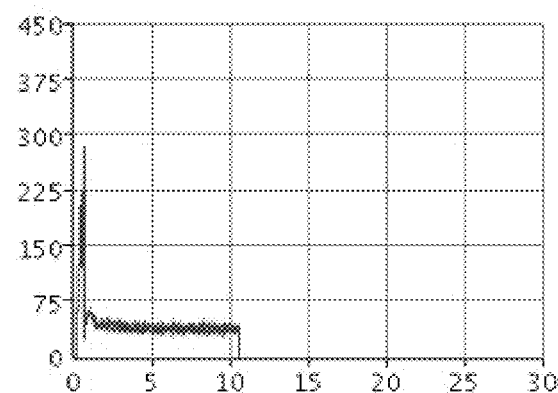

Conjugation of p-SCN-Bn-DTPA to Deoxyribonucleic Acid (DNA) in DMSO with Heating under Microwave 32.4 nmol of a 16mer single-stranded DNA (5'-ATG-GAATTCAGTTCTC-3') was dissolved in 25 µL of 0.5 M NaHCO$_3$ solution. Then, 25 µL of DMSO was added, which contained 1 mg of p-SCN-Bn-DTPA. The reaction was continued for 10 min at 75° C. on a Biotage Initiator microwave heater (see FIGS. 7A and 7B for variations in reaction temperature and power upon heating under microwave). Next, the resulting product was centrifuged for 3 min at 1000 g, and then passed through a Z-25 size exclusion column. Then, the eluate was collected, that is, DTPA-Bn-SCN-DNA. The molecular weight of the product was determined by MALDI-TOF, as shown in FIG. 2. Conjugation of p-SCN-Bn-DTPA to DNA with heating under microwave can provide 100% of DTPA-Bn-SCN-DNA.

EXAMPLE 3

Figure 3:
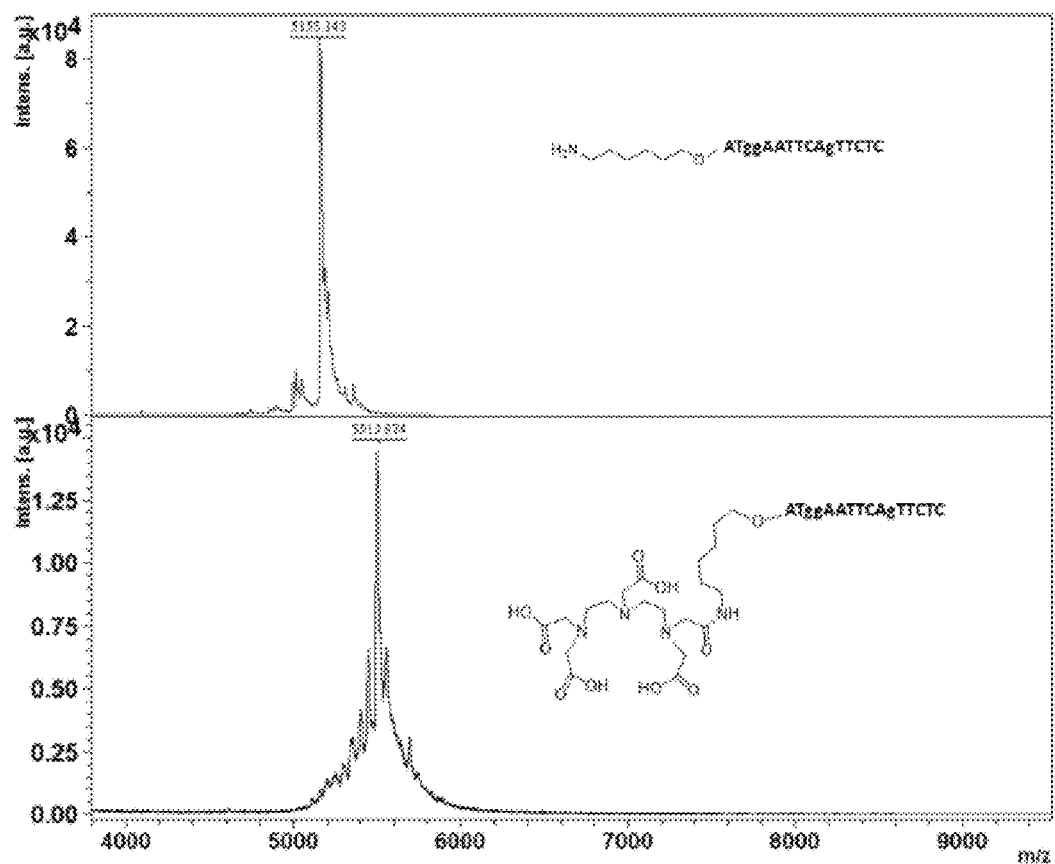
FIG. 3 is a MALDI-TOF mass spectrum of a DTPA anhydride-DNA conjugate prepared in DMSO with heating under microwave.

Conjugation of DTPA Anhydride to DNA in DMSO with Heating under Microwave 32.4 nmol of DNA was back dissolved in 37.5 µL of 0.5 M NaHCO$_3$. 62.5 µL of DMSO was added, which contained 8 mg/mL of DTPA anhydride, and mixed until uniform. The reaction was continued for 10 min at 75° C. on a microwave heater (see FIGS. 7A and 7B for variations in reaction temperature and power upon heating under microwave). Next, the resulting product was centrifuged for 3 min at 1000 g, and then passed through a Z-25 size exclusion column. Then, the eluate was collected, that is, DTPA-DNA. The molecular weight of the product was determined by MALDI-TOF, as shown in FIG. 3. Conjugation of DTPA anhydride to DNA with heating under microwave can provide 100% of DTPA-DNA.

EXAMPLE 4

Figure 4:
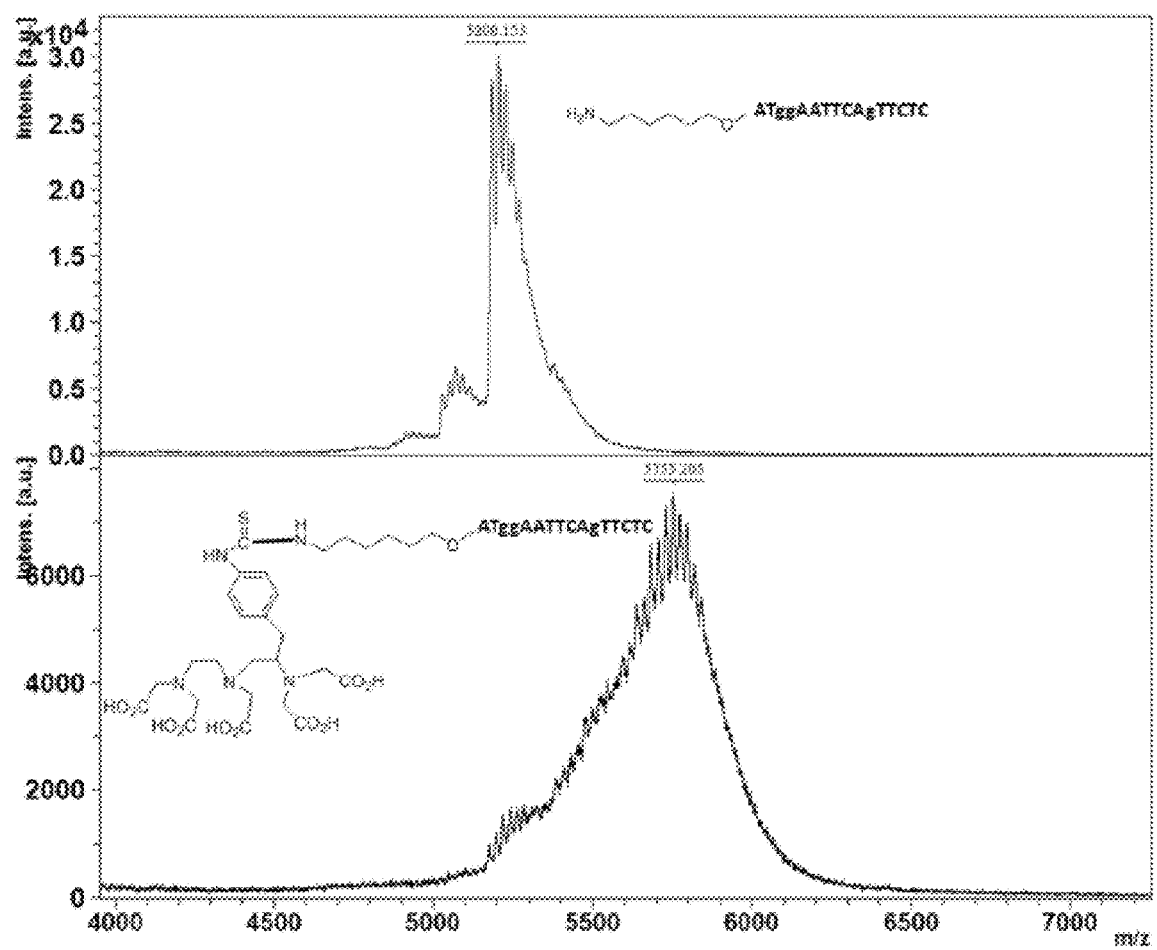
FIG. 4 is a MALDI-TOF mass spectrum of a p-SCN-Bn-DTPA-DNA conjugate prepared in an aqueous phase with heating under microwave.
Figure 6A:
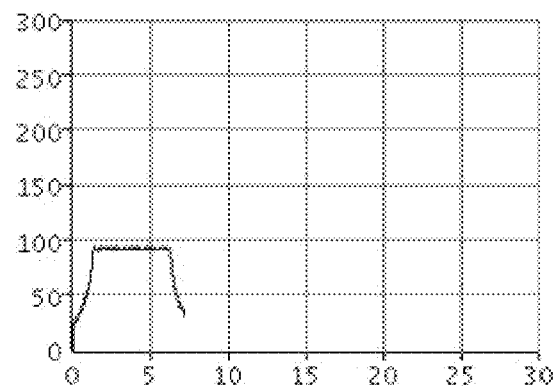
FIGS. 6A and 6B show variations in reaction temperature and power (94° C., 5 min) upon heating under microwave.
Figure 6B:
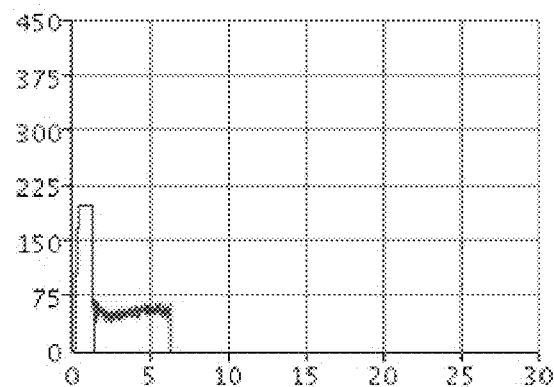

Conjugation of p-SCN-Bn-DTPA to DNA in an Aqueous Phase with Heating under Microwave 10 nmol of DNA was dissolved in 10 µL of double distilled water. 10 µL of 0.5 M NaHCO$_3$ was added, which contained 0.333 mg of p-SCN-Bn-DTPA. Then 30 µL of double distilled water was added to give a total volume of 50 µL, and mixed until uniform. The reaction was continued for 5 min at 94° C. on a microwave heater (see FIGS. 6A and 6B for variations in reaction temperature and power upon heating under microwave). Next, the resulting product was centrifuged for 3 min at 1000 g, and then passed through a Z-25 size exclusion column. Then, the eluate was collected, that is, DTPA-Bn-NCS-DNA. The molecular weight of the product was determined by MS analysis. 100% of DTPA-Bn-SCN-DNA is confirmed to be obtained, as shown in FIG. 4. However, no conjugation occurs when the reaction is carried out in an aqueous at 75° C. for 10 min under microwave.

EXAMPLE 5

Figure 5:
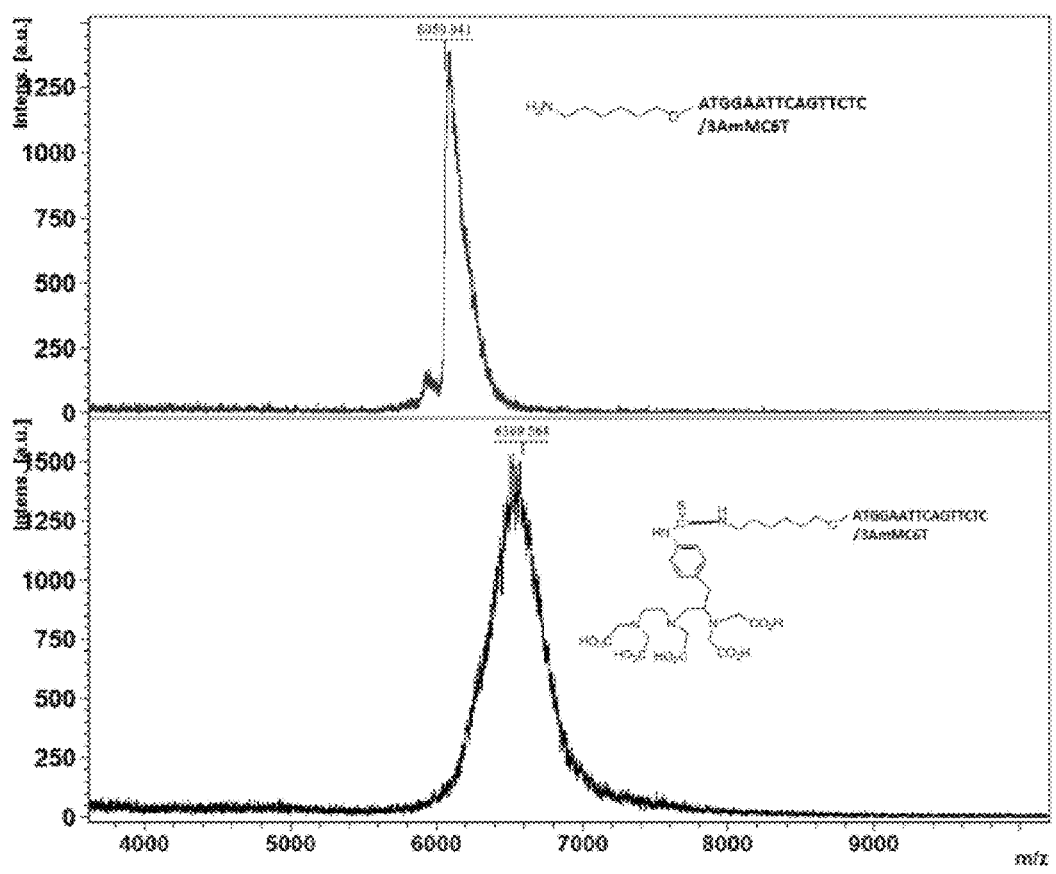
FIG. 5 is a MALDI-TOF mass spectrum of a p-SCN-Bn-DTPA-LNA conjugate prepared in DMSO with heating under microwave.

Conjugation of p-SCN-Bn-DTPA to LNA in DMSO with Heating under Microwave 30 nmol of a 16 mer LNA (5'-ATGGAATTCAGTTCTC-3'; SEQ ID: NO. 1) was dissolved in 25 μL of 0.25 M NaHCO$_3$ solution. 30 μL of DMSO was added, which contained 1 mg of p-SCN-Bn-DTPA. The reaction was continued for 10 min at 75° C. on a Biotage Initiator microwave heater (see FIGS. 7A and 7B for variations in reaction temperature and power upon heating under microwave). Next, the resulting product was centrifuged for 3 min at 1000 g, and then passed through a Z-25 size exclusion column. Then, the eluate was collected, that is, DTPA-Bn-SCN-LNA. The molecular weight of the product was determined by MALDI-TOF, as shown in FIG. 5. Conjugation of p-SCN-Bn-DTPA to LNA with heating under microwave can provide 100% of DTPA-Bn-SCN-LNA.

In summary, the features of the present invention, as a whole or in any combination thereof are neither found in the same type of products, nor previously disclosed, thus meeting the requirements of the patent law. Therefore, this patent of invention is filed in accordance with the patent law.

Embodiments of the present invention are disclosed as above; however, the present invention is not limited thereto. Many variations may be made by any one of skill in the art based on the shape, structure, feature, and spirit described in the claims without departing from the spirit and scope of the present invention. Therefore, the protection scope of the present invention is as defined by the appended claims.

---

---

What is claimed is:

1. A high-yield method for rapidly conjugating a nucleic acid to a diethylenetriamine pentaacetic acid (DTPA) derivative, wherein the nucleic acid is a ribonucleic acid (RNA), deoxyribonucleic acid (DNA) or locked nucleic acid (LNA), and the method comprises the steps of:
reacting the nucleic acid and the DTPA derivative for 5 min at 94° C. in an aqueous sodium bicarbonate solution or for 10 min at 75° C. in a 2-10% sodium bicarbonate solution in DMSO, with heating under microwave, wherein the DTPA derivative is a DTPA anhydride or p-isothiocyanate benzyl-DTPA (SCN-Bn-DTPA).

2. The method according to claim 1, wherein the pH of the sodium bicarbonate solution is 8.0-8.5.

3. The method according to claim 1, wherein the nucleic acid is the LNA or DNA having an amino group.

4. The method according to claim 1, wherein the nucleic acid is the RNA which is at nmol level.

5. The method according to claim 4, wherein the reaction yield of the RNA-DTPA conjugate is 100%.

* * * * *

SEQUENCE LISTING

```
<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<223> OTHER INFORMATION: ssDNA

<400> SEQUENCE: 1
atggaattca gttctc                                                     16
```